US012697323B2

(12) United States Patent
Freehauf et al.

(10) Patent No.: US 12,697,323 B2
(45) Date of Patent: Aug. 4, 2026

(54) IMPLANTABLE ISOXAZOLINE PHARMACEUTICAL COMPOSITIONS AND USES THEREOF

(71) Applicant: Intervet Inc., Madison, NJ (US)

(72) Inventors: Keith Freehauf, Stockton, NJ (US); Anagha Avinash Bhakay, Fanwood, NJ (US)

(73) Assignee: Intervet Inc., Rahway, NJ (US)

( * ) Notice: Subject to any disclaimer, the term of this patent is extended or adjusted under 35 U.S.C. 154(b) by 424 days.

(21) Appl. No.: 18/295,616

(22) Filed: Apr. 4, 2023

(65) Prior Publication Data

US 2023/0233530 A1 Jul. 27, 2023

Related U.S. Application Data

(62) Division of application No. 16/769,509, filed as application No. PCT/EP2018/084276 on Dec. 11, 2018, now Pat. No. 11,648,238.

(60) Provisional application No. 62/597,663, filed on Dec. 12, 2017.

(51) Int. Cl.

| | |
|---|---|
| ***A61K 31/42*** | (2006.01) |
| ***A61K 9/00*** | (2006.01) |
| ***A61K 9/16*** | (2006.01) |
| ***A61K 9/20*** | (2006.01) |
| ***A61K 9/50*** | (2006.01) |
| ***A61K 47/02*** | (2006.01) |
| ***A61K 47/10*** | (2017.01) |
| ***A61K 47/12*** | (2006.01) |

(52) U.S. Cl.

CPC ............ *A61K 31/42* (2013.01); *A61K 9/0024* (2013.01); *A61K 9/1623* (2013.01); *A61K 9/1635* (2013.01); *A61K 9/1641* (2013.01); *A61K 9/2081* (2013.01); *A61K 9/5031* (2013.01); *A61K 47/02* (2013.01); *A61K 47/10* (2013.01); *A61K 47/12* (2013.01)

(58) Field of Classification Search

None

See application file for complete search history.

(56) References Cited

U.S. PATENT DOCUMENTS

| | | | |
|---|---|---|---|
| RE39,592 E | 4/2007 | Cady et al. |
| 7,767,708 B2 | 8/2010 | Chung et al. |
| 7,999,005 B2 | 8/2011 | Shih et al. |
| 9,259,417 B2 | 2/2016 | Soll et al. |
| 9,655,884 B2 | 5/2017 | Williams et al. |
| 2007/0066617 A1 | 3/2007 | Mita et al. |
| 2017/0295789 A1 | 10/2017 | Mitsudera et al. |

FOREIGN PATENT DOCUMENTS

| | | | |
|---|---|---|---|
| EP | 0990450 | A2 | 4/2000 |
| WO | 2005085216 | A1 | 9/2005 |
| WO | 2007079162 | A1 | 7/2007 |
| WO | 2009002809 | A2 | 12/2008 |
| WO | 2009003075 | A1 | 12/2008 |
| WO | 2009024541 | A2 | 2/2009 |
| WO | 2010070068 | A2 | 6/2010 |
| WO | 2010079077 | A1 | 7/2010 |
| WO | 2013008218 | A1 | 1/2013 |
| WO | 2015048371 | A1 | 4/2015 |
| WO | 2015086551 | A1 | 6/2015 |
| WO | 2016164487 | A1 | 10/2016 |
| WO | 2018081733 | A1 | 5/2018 |

OTHER PUBLICATIONS

U.S. Appl. No. 16/769,509, filed Jun. 3, 2020.

*Primary Examiner* — Anna R Falkowitz
(74) *Attorney, Agent, or Firm* — David J. Kerwick

(57) ABSTRACT

An implant for the control of parasites in livestock comprising an isoxazoline compound of Formula (I)

Formula (I)

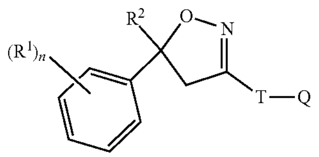

or salt or solvate thereof, wherein the implant comprises one or more pellets each of which comprises the isoxaxoline compound and a pharmaceutically acceptable excipient and a method of preventing or treating a parasite infestation using the same.

9 Claims, 3 Drawing Sheets

IMPLANTABLE ISOXAZOLINE PHARMACEUTICAL COMPOSITIONS AND USES THEREOF

CROSS-REFERENCE TO RELATED APPLICATIONS

This application is a divisional application of U.S. application Ser. No. 16/769,509, filed Jun. 3, 2020, which is a U.S. National Phase entry under 35 U.S.C. § 371 of PCT/EP2018/084276 filed on Dec. 11, 2018, which claims priority under 35 U.S.C. § 119 (e) of provisional application U.S. Ser. No. 62/597,663 filed Dec. 12, 2017, the contents of which are hereby incorporated by reference in their entireties.

BACKGROUND

Isoxazoline compounds are known in the art and these compounds and their use as antiparasitic are described, for example, in US patent application US 2007/0066617, and International Patent applications WO 2005/085216, WO 2007/079162, WO 2009/002809, WO 2009/024541, WO 2009/003075, WO 2010/070068 and WO 2010/079077, the disclosures of which, as well as the references cited herein, are incorporated by reference. This class of compounds is known to possess excellent activity against ectoparasites, i.e. parasitic insect and acarids, such as fleas and ticks and endoparasites such as nematodes.

Examples of isoxazoline compounds are carbamoyl benzamide phenyl isoxazoline (CBPI) compounds. A specific example of a CBPI compound is 4-[5-(3,5-Dichlorophenyl)-5-trifluoromethyl-4,5-dihydroisoxazol-3-yl]-2-methyl-N-[(2,2,2-trifluoro-ethylcarbamoyl)-methyl]-benzamide (CAS RN [864731-61-3])—USAN fluralaner.

fluralaner

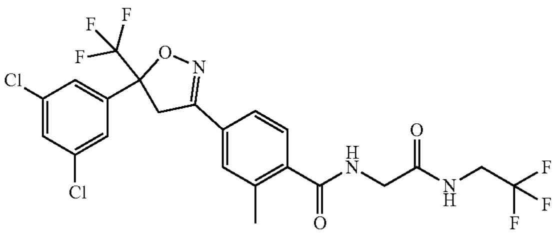

The CBPI compound fluralaner is disclosed in patent application WO 2005/085216.

U.S. Pat. No. 9,655,884 discloses methods of preventing re-infestation of animals by fleas comprising administering an isoxazoline compound including fluralaner. The systemic administration of isoxazoline compounds by subcutaneous implants is also disclosed. There is no disclosure of the composition of the implants or the release profile of the isoxazoline compound once implanted.

U.S. Reissued Pat. No. RE 39,592 discloses extended release implants comprising growth promoters and a biodegradable polymer. There is no disclosure of implants comprising isoxazolines.

U.S. Pat. Nos. 7,767,708 and 7,999,005 disclose implants comprising growth promoting compounds in an immediate release formulation and in a controlled release formulation. There is no disclosure of implants comprising isoxazolines.

SUMMARY OF THE INVENTION

An implant for the control of parasites in livestock comprising an isoxazoline compound of Formula (I)

(Formula I)

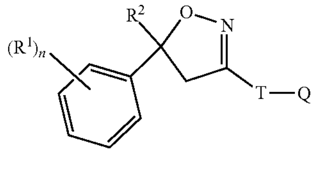

wherein $R^1$=halogen, $CF_3$, $OCF_3$, or CN;

n=integer from 0 up to and including 3;

m=1 or 2;

$R^2$=$C_1$-$C_3$ haloalkyl;

T=ring structure: 5-, or 6-membered, or bicyclic, which is optionally substituted by one or more radicals Y;

Y=methyl, halomethyl, halogen, CN, $NO_2$, $NH_2$—C═S, or two adjacent radicals Y together form a chain;

Q=X—$NR^3R^4$, $NR^5$—$NR^6$—X—$R^3$, X—$R^3$, or a 5-membered N-heteroaryl ring, which is optionally substituted by one or more radicals;

X=$CH_2$, $CH(CH_3)$, CH(CN), CO, CS;

$R^3$=hydrogen, methyl, haloethyl, halopropyl, halobutyl, methoxymethyl, methoxyethyl, halomethoxymethyl, ethoxymethyl, haloethoxymethyl, propoxymethyl, ethylaminocarbonylmethyl, ethylaminocarbonylethyl, dimethoxyethyl, propynylaminocarbonylmethyl, N-phenyl-N-methyl-amino, haloethylaminocarbonylmethyl, haloethylaminocarbonylethyl, tetrahydrofuryl, methylaminocarbonylmethyl, (N,N-dimethylamino)-carbonylmethyl, propylaminocarbonylmethyl, cyclopropylaminocarbonylmethyl, propenylaminocarbonylmethyl, haloethylaminocarbonylcyclopropyl, alkylsulfanylalkyl, alkylsulfinylalkyl, alkylsulfonylalkyl, cycloalkyl, $R^3$-1

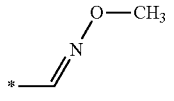

$R^3$-2

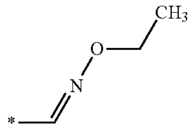

$R^3$-3

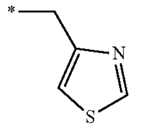

$R^3$-4

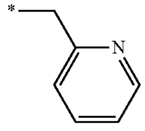

-continued $R^3$-5

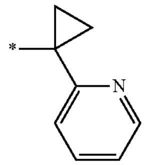

$R^3$-6

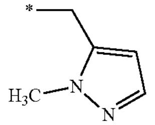

$R^3$-7

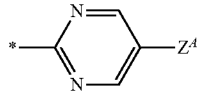

$R^3$-8

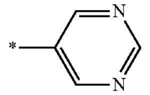

$R^3$-9

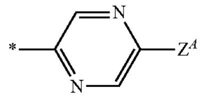

$R^3$-10

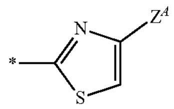

$R^3$-11

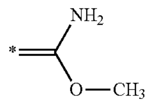

$R^3$-12

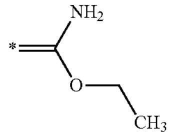

$R^3$-13

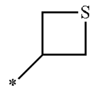

$R^3$-14

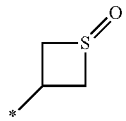

$R^3$-15

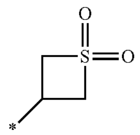

$R^3$-16

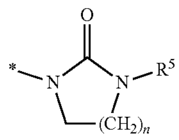

-continued $R^3$-17

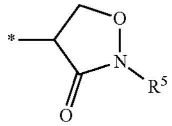

or $R^3$-18

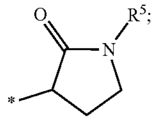

wherein $Z^A$=hydrogen, halogen, cyano, or halomethyl ($CF_3$);

$R^4$=hydrogen, ethyl, methoxymethyl, halomethoxymethyl, ethoxymethyl, haloethoxymethyl, propoxymethyl, methylcarbonyl, ethylcarbonyl, propylcarbonyl, cyclopropylcarbonyl, methoxycarbonyl, methoxymethylcarbonyl, aminocarbonyl, ethylaminocarbonylmethyl, ethylaminocarbonylethyl, dimethoxyethyl, propynylaminocarbonylmethyl, haloethylaminocarbonylmethyl, cyanomethylaminocarbonylmethyl, or haloethylaminocarbonylethyl;

$R^5$=H, alkyl, or haloalkyl;

$R^6$=H, alkyl, or haloalkyl;

or wherein $R^3$ and $R^4$ together form a substituent selected from the group consisting of:

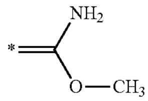

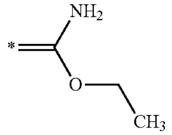

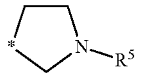

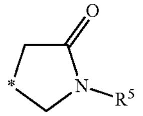

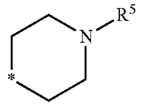

and

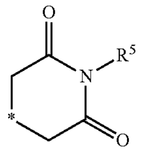

or salt or solvate thereof, wherein the implant comprises one or more pellets and each pellet comprises the isoxaxoline compound and one or more pharmaceutically acceptable excipients.

Another embodiment is a method of treating or preventing a parasite infestation in livestock animals comprising administering the above implant to animals in need thereof.

DETAILED DESCRIPTION

Figure 1:
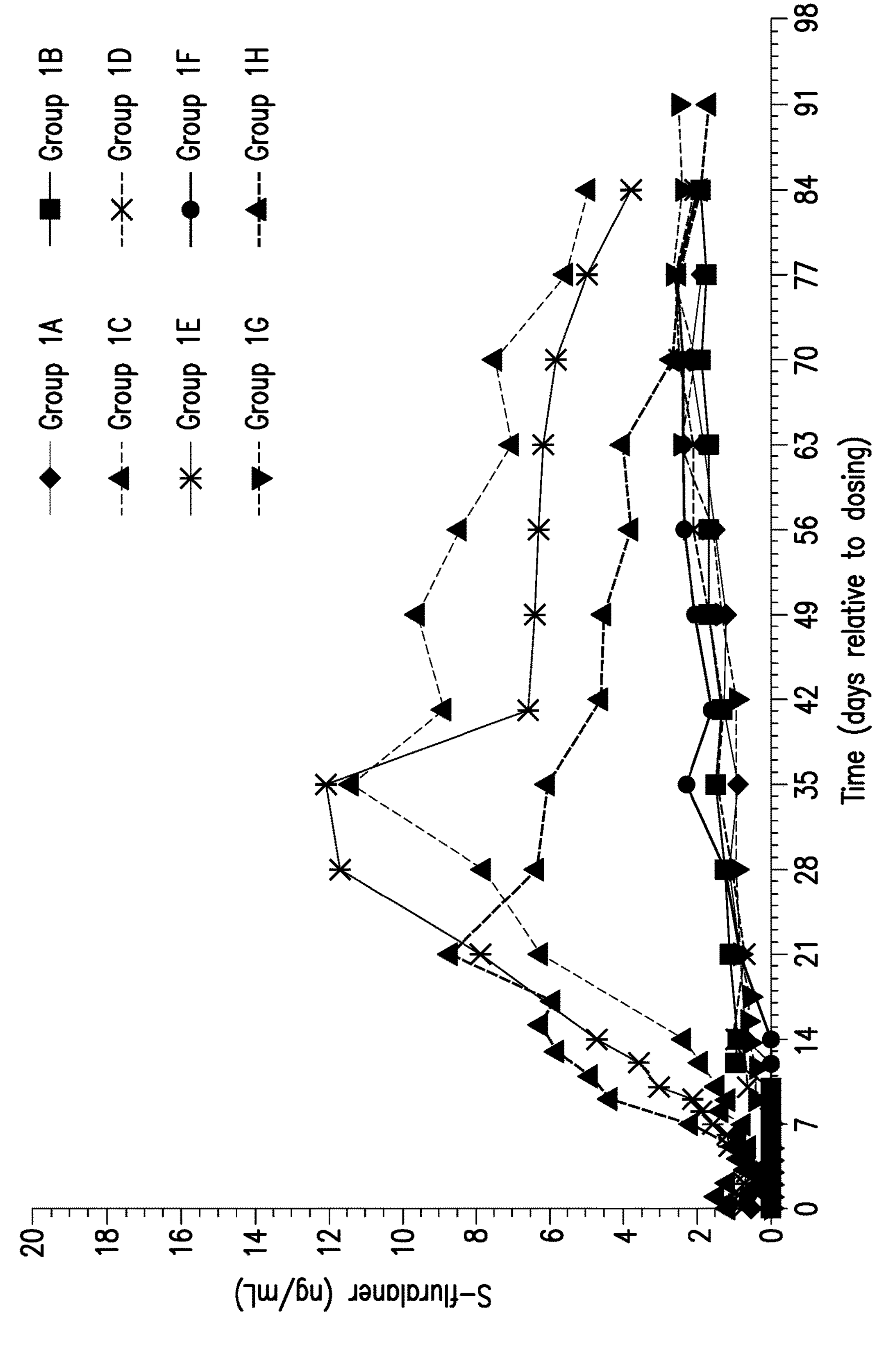
FIG. 1—Pharmacokinetic (PK) study data from animals implanted with the pellets of Formulations 1A to 1H.
Figure 2:
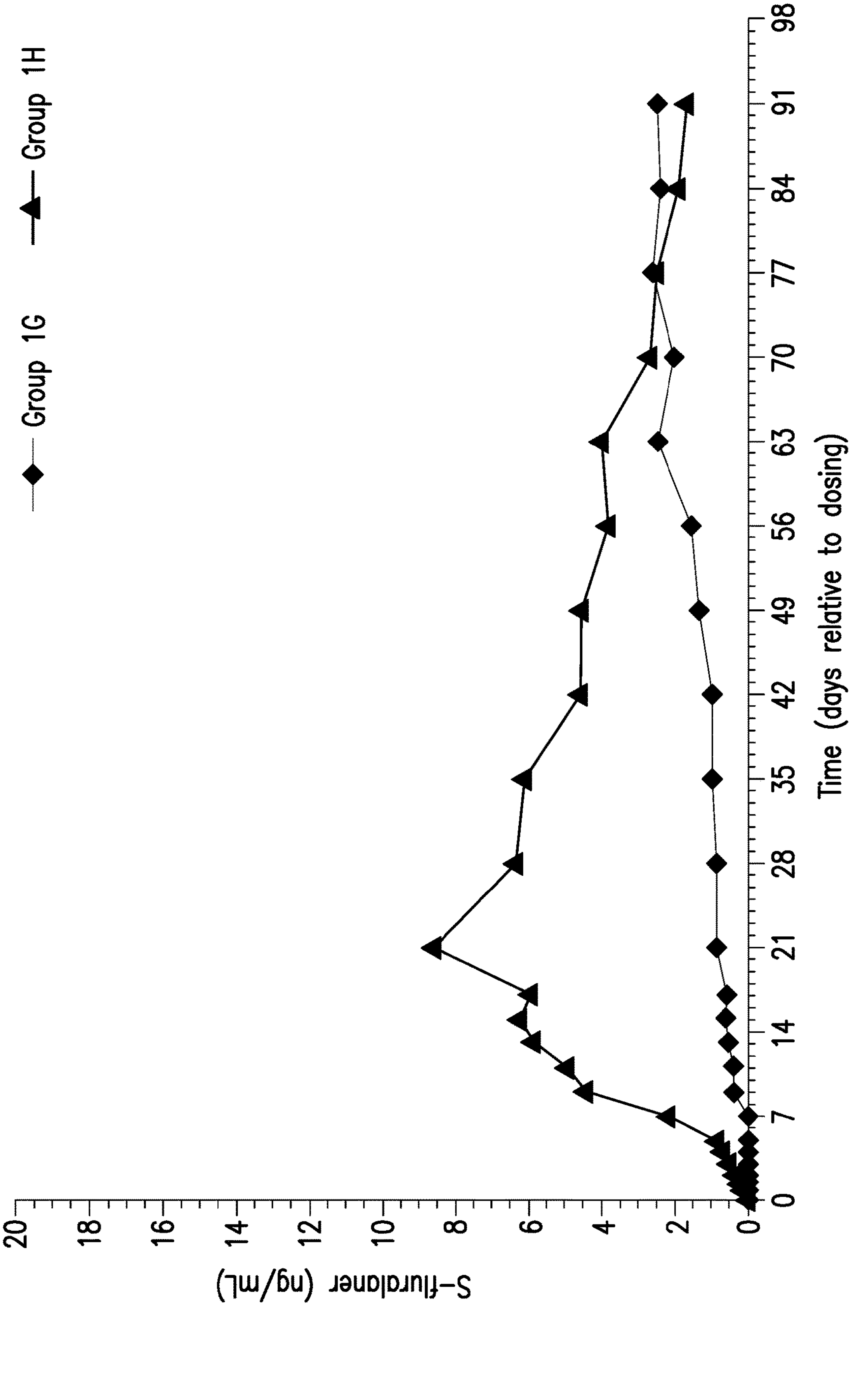
FIG. 2—Pharmacokinetic (PK) study data from animals implanted with delayed release pellets of Formulation 1G and immediate release pellets of Formulation 1H FIG. 3—Pharmacokinetic (PK) study data from animals implanted with the pellets of Formulations 3A to 3G.

Implant technology is well accepted and widespread in the areas of animal health and production enhancement. Growth stimulants are commonly used to enhance the body weight of animals which are raised for slaughtering, such as cattle, swine, sheep, and the like.

In the case of cattle, swine and sheep, growth stimulants are administered as solid pellets which are injected by an implanter equipped with a hypodermic needle. The needle is used to make a surface self-sealing and, non-coring implant receiving puncture beneath the skin of the ear of the animal. Small pellets of growth hormone are forced through the needle and left under the skin as the needle is removed from the ear. The ears are commonly discarded in slaughtering, such that no unabsorbed residues of such pellets will end up in food products intended for humans.

The pellets are administered to the animal by an implanter apparatus subcutaneously through the bore of a hypodermic needle which is remotely coupled to a pellet magazine. Such pellet magazine comprises a plurality of pellets sized to be implanted through the needle and positioned in the magazine for selective alignment of a pellet with the needle.

In one embodiment the pellets include at least one dose of an isoxazoline compound of formula (I) for immediate release in the first pellet and at least one dose of an isoxazoline compound of formula (I) dose of delayed release in the second pellet which combined pellets are packaged in the magazine in sequential order for simultaneous delivery of the immediate release and delayed release dose as part of a single injection.

Therefore in one embodiment the current invention provides method of protecting an animal, especially a livestock animal, especially a cattle (or bovid) animal from parasite infestation; said method comprising the steps of:

(a) providing an implanter apparatus for implanting pharmaceutical pellets in an animal through the bore of a hypodermic needle which is operably coupled to a pellet magazine;
(b) loading the pellet magazine with an immediate release pharmaceutical pellet dose comprising an isoxazoline compound of formula (I) in a first pellet and delayed release pellet dose comprising an isoxazoline compound of formula (I) in a second pellet; said first and second pellets being separate and discrete;
(c) inserting the hypodermic needle under the skin of the animal and implanting said immediate release dose and said delayed dose in a single injection; and
(d) withdrawing the hypodermic needle from under the skin of the animal so as to leave immediate release dose and said delayed dose in beneath the skin of the animal.

In another embodiment such method includes the step of providing a plurality of discrete pellet doses.

In another embodiment an implant for subcutaneous implantation in an animal is provided comprising:

(a) at least one discrete immediate release pharmaceutical pellet dose comprising an isoxazoline compound of formula (I); and
(b) at least one discrete delayed release pellet dose comprising an isoxazoline compound of formula (I); all of said pellets being combined in a single unit for implantation side by side into the same site.

Definitions

Pharmaceutically acceptable excipient is an inert substance that forms a vehicle or medium for a drug.

Disintegrants are implant excipients that help to break (disintegrate) an implant. Most disintegrants swell on contact with water which exerts force on the tablet causing the implant to break. Examples of disintegrants: sodium starch glycolate (SSG), croscarmellose sodium (CCS), and crospovidone (crosslinked polyvinylpyrrolidone).

Diluent means the substance used to dilute a mixture, a suspension or a solution.

Binder is an agent used to impart cohesive qualities to powdered material.

Lubricant is an agent used to prevent adhesion of the solid material to the surface of manufacturing equipment (e.g. dies and punches), to reduce interparticle friction and to improve rate of flow of the granulation.

Surfactant means a surface active agent or one that affects the surface tension.

Anti-tacking agent is a substance that prevents coated pellets from sticking to one another.

A parasite "infestation" refers to the presence of parasites in numbers that pose a risk to humans or animals. The presence can be in the environment, e.g., in animal bedding, on the skin or fur of an animal, etc. When the infestation that is referred to is within an animal, e.g., in the blood or other internal tissues, the term infestation is also intended to be synonymous with the term, "infection," as that term is generally understood in the art, unless otherwise stated.

Livestock are bovids, such as cattle animals, especially beef cattle, sheep, goats and pigs.

Isoxazoline compounds are known in the art and compounds from this class are known to possess excellent activity against parasite infestations such as ticks, fleas, lice and other ectoparasties. Embodiments of the subject invention are provided below.

Isoxazolines used with this invention may be in the form of a salt. A salt may be advantageous due to one or more of its physical properties, such as pharmaceutical stability in differing temperatures and humidities; crystalline properties; and/or a desirable solubility in water, oil, or other solvents. Acid and base salts typically can be formed by, for example, mixing a compound with an acid or base, respectively, using various known methods in the art. In general, when the salt is intended to be administered in vivo (i.e., to an animal) for a therapeutic benefit, the salt preferably is pharmaceutically acceptable.

The isoxazolines of Formula (I) are in the form of stable complexes with solvent molecules that remain intact after the non-complexed solvent molecules are removed from the compounds. These complexes generally are referred to as "solvates." In some instances, the solvate will be capable of isolation, for example when one or more solvent molecules are incorporated into the crystal lattice of the crystalline solid. A "solvate" encompasses both solution-phase and isolatable solvates. Examples of suitable solvates include ethanolates, methanolates, and the like. A "hydrate" is a solvate wherein the solvent molecule is water. A solvate intended to be used in vivo preferably is pharmaceutically acceptable.

The pellets of the implant have the shape of a cylindrical tablet having a diameter of about 2.0 mm to about 6.0 mm and a length of about 1.0 mm to about 8.0 mm. The expression "conventional release" or "immediate release" refers to the uncontrolled release of the drug into the blood of the animal resulting in a short duration of action. The initial levels of the drug in the blood are initially low, rapidly rising and then rapidly falling off (see U.S. Pat. No. RE 39,592).

Sustained release refers to the slow release of a drug into the blood stream of the animal over a prolonged period of time wherein the blood levels of the drug decline rapidly over time but not as rapidly as in the convention release (see U.S. Pat. No. RE 39,592).

Delayed release refers to the release of a drug into the blood of animal after an induction period subsequent to the administration of the drug, without an initial burst.

In the context of this invention, the isoxazoline in the delayed release pellets should be released so as to obtain a blood level of the isoxazoleine to be effective against the target parasites in about 40 days, preferably about 60 days and be sustained at least that level for an additional 30 to 120 days.

Immediate release refers to the near term release of a drug in the blood stream of the animal over a short period of time wherein the blood levels of the drug decline over time more rapidly than as in the delayed release.

In the context of this invention, the isoxazoline in the immediate release pellets are preferred to be released so as to obtain a blood level of the isoxazoline to be effective against the target parasites in less than 7 days and be sustained at least that level for an additional 50 to 60 days.

In the context of this invention, the terms intra granular and extra granular refer to the order in the process of making the implant pellets when the surfactant (e.g. poloxamer) is introduced. In both situations, a small portion of the surfactant is dissolved in the binder (e.g. povidone) solution. In the intra granular version, the remainder of the surfactant is combined with the isoxazoline compound and the diluent (e.g. lactose). This mixture is then combined with the binder solution to form granules which are then compressed into pellets. In the extra granular version, the granules are formed by mixing the isoxazoline compound, the diluent and the binder solution. Once the granules have formed, then the remaining surfactant is blended with the granules. The resulting blend is then compressed into pellets.

Micronized means to reduce a substance to a fine powder with particles whose sizes (dimensions) are measured in microns (μm) ($10^{-6}$ meters) of less 10 μm or preferably less than 5 μm.

Poloxamers are nonionic triblock copolymers composed of a central hydrophobic chain of polyoxypropylene (poly (propylene oxide)) flanked by two hydrophilic chains of polyoxyethylene (poly(ethylene oxide)) (see U.S. Pat. No. 3,740,421).

Poloxamer 124 is poly(ethylene glycol)-block-poly(propylene glycol)-block-poly(ethylene glycol, CAS Number 9003-11-6. Also known as Lutrol L44 or Kollisolv P124.

Lutrol F68 is another poly(ethylene glycol)-block-poly (propylene glycol)-block-poly(ethylene glycol), Also known as Poloxamer 188 or Kolliphor P188. This poloxamer has an average molecular weight in the range of about 7680 to 9510.

Poloxamer 407 is another poly(ethylene glycol)-block-poly(propylene glycol)-block-poly(ethylene glycol). Also known as Pluronic 127. This poloxamer has an average molecular weight in the range of about 9840 to 14,600.

Povidone is a water-soluble polymer made from the monomer N-vinylpyrrolidone

Biodegradable polymer refers to those synthetic and naturally occurring water-insoluble polymers that degrade by hydrolysis or enzymatic processes. Examples include but are not limited to poly(lactic-co-glycolic acid) (PLGA) and polycaprolactone (PCL)(see U.S. Pat. No. RE 39,592).

Systemic administration of medicaments means that the target (organ or parasite) is reached via the bloodstream.

In an embodiment of an isoxazoline for use in the invention, T is selected from

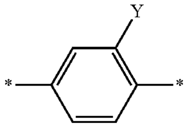
T-1

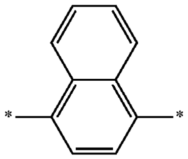
T-2

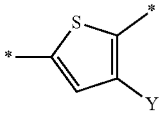
T-3

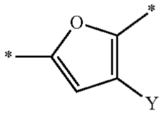
T-4

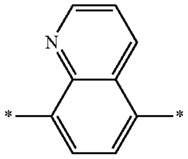
T-5

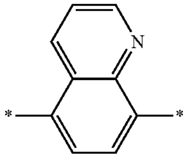
T-6

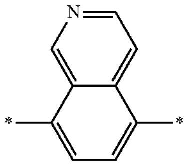
T-7

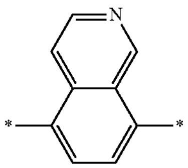
T-8

-continued
T-9
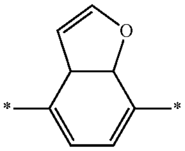
T-10
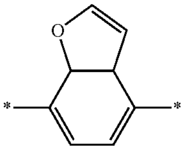
T-11
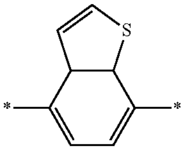
T-12
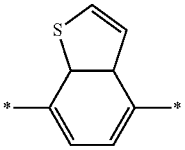
T-13
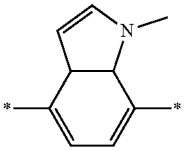
T-14
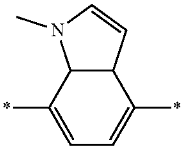
T-15
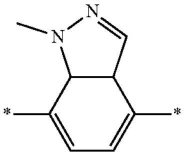
T-16
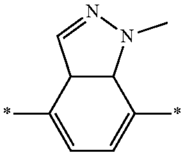
T-17
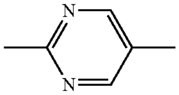
T-18
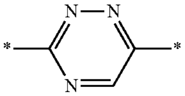
T-19
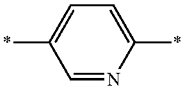
-continued
T-20
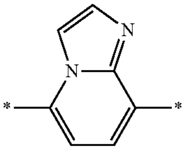
T-21
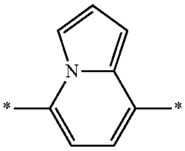
T-22
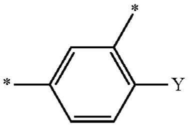
T-23
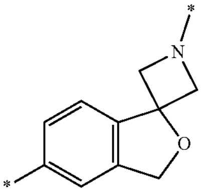
T-24
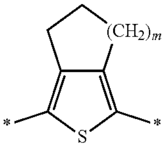
T-25
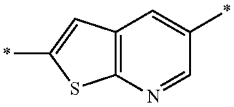
wherein in T-1, T-3 and T-4, the radical Y=hydrogen, halogen, methyl, halomethyl, ethyl, or haloethyl.
In an embodiment of an isoxazoline for use in the invention, Q is selected from
Q-1
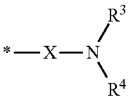
Q-2
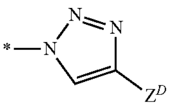
Q-3
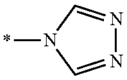
Q-4
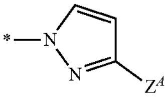

-continued
Q-5
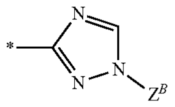
Q-6
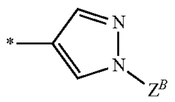
Q-7
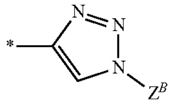
Q-8
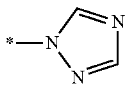
Q-9
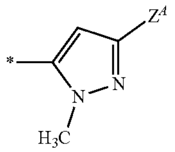
wherein $R^3$, $R^4$, X and $Z^A$ are as defined above, and
$Z^B$=
$Z^B$-1
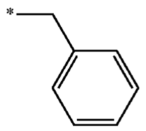
$Z^B$-2
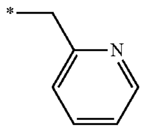
$Z^B$-3
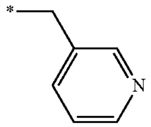
$Z^B$-4
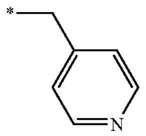
$Z^B$-5
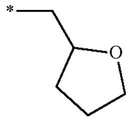
$Z^B$-6
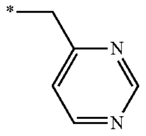
-continued
$Z^B$-7
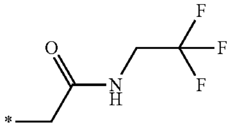
$Z^B$-8
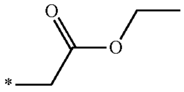
$Z^B$-9
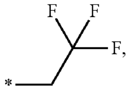
$Z^D$=
$Z^D$-1
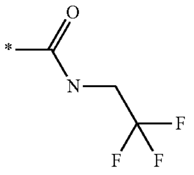
$Z^D$-2
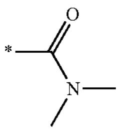
$Z^D$-3
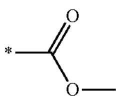
$Z^D$-4
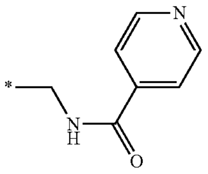
$Z^D$-5
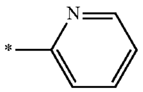
$Z^D$-6
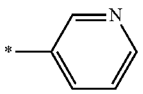
In an embodiment an isoxazoline for use in the invention is as presented in Table 1.

TABLE 1

| $(R^1)_n$ | $R^2$ | $R^3$ | $R^4$ | T | Y | Q | Z | X |
|---|---|---|---|---|---|---|---|---|
| 3-Cl, 5-Cl | $CF_3$ | $CH_2CF_3$ | H | T-2 | — | Q-1 | — | CO |
| 3-Cl, 5-Cl | $CF_3$ | $CH_2CH_3$ | H | T-2 | — | Q-1 | — | CO |
| 3-Cl, 5-Cl | $CF_3$ | $CH_2CH_2OCH_3$ | H | T-2 | — | Q-1 | — | CO |
| 3-Cl, 5-Cl | $CF_3$ | $CH_2C(O)NHCH_2CF_3$ | H | T-2 | — | Q-1 | — | CO |
| 3-Cl, 5-Cl | $CF_3$ | $CH_2C(O)NHCH_2CH_3$ | H | T-2 | — | Q-1 | — | CO |
| 3-$CF_3$, 5-$CF_3$ | $CF_3$ | $CH_2C(O)NHCH_2CF_3$ | H | T-2 | — | Q-1 | — | CO |
| 3-$CF_3$, 5-$CF_3$ | $CF_3$ | $CH_2C(O)NHCH_2CH_3$ | H | T-2 | — | Q-1 | — | CO |
| 3-$CF_3$, 5-Cl | $CF_3$ | $CH_2C(O)NHCH_2CF_3$ | H | T-2 | — | Q-1 | — | CO |
| 3-$CF_3$, 5-Cl | $CF_3$ | $CH_2C(O)NHCH_2CH_3$ | H | T-2 | — | Q-1 | — | CO |
| 3-Cl, 5-Cl | $CF_3$ | — |  | T-2 | — | Q-6 | $Z^B$-7 | CO |
| 3-Cl, 5-Cl | $CF_3$ | — | — | T-2 | — | Q-7 | $Z^B$-7 | CO |
| 3-Cl, 5-Cl | $CF_3$ | — | — | T-2 | — | Q-5 | $Z^B$-7 | CO |
| 3-Cl, 5-Cl | $CF_3$ | — | — | T-2 | — | Q-2 | $Z^D$-1 | CO |
| 3-Cl, 5-Cl | $CF_3$ | $CH_2C(O)NHCH_2CF_3$ | H | T-3 | $CH_3$ | Q-1 | — | CO |
| 3-Cl, 5-Cl | $CF_3$ | $CH_2C(O)NHCH_2CC$ | H | T-3 | $CH_3$ | Q-1 | — | CO |
| 3-Cl, 5-Cl | $CF_3$ | $CH_2C(O)NHCH_2CN$ | H | T-3 | $CH_3$ | Q-1 | — | CO |
| 3-Cl, 5-Cl | $CF_3$ | $CH_2C(O)NHCH_2CH_3$ | H | T-3 | $CH_3$ | Q-1 | — | CO |
| 3-$CF_3$, 5-$CF_3$ | $CF_3$ | $CH_2C(O)NHCH_2CF_3$ | H | T-3 | $CH_3$ | Q-1 | — | CO |
| 3-$CF_3$, 5-$CF_3$ | $CF_3$ | $CH_2C(O)NHCH_2CH_3$ | H | T-3 | $CH_3$ | Q-1 | — | CO |
| 3-Cl, 4-Cl, 5-Cl | $CF_3$ | $CH_2C(O)NHCH_2CF_3$ | H | T-3 | $CH_3$ | Q-1 | — | CO |
| 3-Cl, 4-Cl, 5-Cl | $CF_3$ | $CH_2C(O)NHCH_2CH_3$ | H | T-3 | $CH_3$ | Q-1 | — | CO |
| 3-Cl, 4-F, 5-Cl | $CF_3$ | $CH_2C(O)NHCH_2CF_3$ | H | T-3 | $CH_3$ | Q-1 | — | CO |
| 3-Cl, 4-F, 5-Cl | $CF_3$ | $CH_2C(O)NHCH_2CH_3$ | H | T-3 | $CH_3$ | Q-1 | — | CO |
| 3-Cl, 5-Cl | $CF_3$ | $CH_2C(O)NHCH_2CF_3$ | H | T-20 | — | Q-1 | — | CO |
| 3-Cl, 5-Cl | $CF_3$ | $CH_2C(O)NHCH_2CH_3$ | H | T-20 | — | Q-1 | — | CO |
| 3-$CF_3$, 5-$CF_3$ | $CF_3$ | $CH_2C(O)NHCH_2CF_3$ | $CH_3$ | T-20 | — | Q-1 | — | CO |
| 3-$CF_3$, 5-$CF_3$ | $CF_3$ | $CH_2C(O)NHCH_2CH_3$ | $CH_3$ | T-20 | — | Q-1 | — | CO |
| 3-$CF_3$, 5-$CF_3$ | $CF_3$ | $CH_2C(O)NHCH_2CF_3$ | H | T-20 | — | Q-1 | — | CO |
| 3-$CF_3$, 5-$CF_3$ | $CF_3$ | $CH_2C(O)NHCH_2CH_3$ | H | T-20 | — | Q-1 | — | CO |
| 3-$CF_3$, 5-$CF_3$ | $CF_3$ | $CH_2C(O)NHCH_2CF_3$ | H | T-21 | — | Q-1 | — | CO |
| 3-$CF_3$, 5-$CF_3$ | $CF_3$ | $CH_2C(O)NHCH_2CH_3$ | H | T-21 | — | Q-1 | — | CO |
| 3-Cl, 5-Cl | $CF_3$ | $CH_2C(O)NHCH_2CF_3$ | H | T-21 | — | Q-1 | — | CO |
| 3-Cl, 5-Cl | $CF_3$ | $CH_2C(O)NHCH_2CH_3$ | H | T-21 | — | Q-1 | — | CO |
| 3-Cl, 5-Cl | $CF_3$ | $CH_2CH_2SCH_3$ | H | T-21 | — | Q-1 | — | CO |
| 3-Cl, 4-Cl, 5-Cl | $CF_3$ | $C(O)CH_3$ | H | T-22 | F | Q-1 | — | $CH_2$ |
| 3-Cl, 4-Cl, 5-Cl | $CF_3$ | $C(O)CH(CH_3)_2$ | H | T-22 | F | Q-1 | — | $CH_2$ |
| 3-Cl, 4-Cl, 5-Cl | $CF_3$ | C(O)-cyclo-propyl | H | T-22 | F | Q-1 | — | $CH_2$ |
| 3-Cl, 4-F, 5-Cl | $CF_3$ | $C(O)CH_3$ | H | T-22 | F | Q-1 | — | $CH_2$ |
| 3-Cl, 4-Cl, 5-Cl | $CF_3$ | $C(O)CH_2CH_3$ | H | T-22 | F | Q-1 | — | $CH_2$ |
| 3-Cl, 4-F, 5-Cl | $CF_3$ | $C(O)CH_3$ | H | T-22 | Cl | Q-1 | — | $CH_2$ |
| 3-Cl, 5-Cl | $CF_3$ | $CH_2C(O)NHCH_2CF_3$ | H | T-1 | $CH_3$ | Q-1 | — | CO |
| 3-Cl, 5-Cl | $CF_3$ | $CH_2C(O)NHCH_2CH_3$ | H | T-1 | $CH_3$ | Q-1 | — | CO |
| 3-Cl, 5-Cl | $CF_3$ | $R^3$-1 (Z) | H | T-1 | $CH_3$ | Q-1 | — | CO |
| 3-Cl, 5-Cl | $CF_3$ | $R^3$-1 (E) | H | T-1 | $CH_3$ | Q-1 | — | CO |

In an embodiment an isoxazoline for use in the invention is as presented in Table 2.

TABLE 2

| $(R^1)_n$ | $R^2$ | $R^3$ | $R^4$ | T | Y | Q | Z | X |
|---|---|---|---|---|---|---|---|---|
| 3-Cl, 5-Cl | $CF_3$ | $CH_2CF_3$ | H | T-2 | — | Q-1 | — | CO |
| 3-Cl, 5-Cl | $CF_3$ | $CH_2CH_3$ | H | T-2 | — | Q-1 | — | CO |
| 3-Cl, 5-Cl | $CF_3$ | $CH_2CH_2OCH_3$ | H | T-2 | — | Q-1 | — | CO |
| 3-Cl, 5-Cl | $CF_3$ | $CH_2C(O)NHCH_2CF_3$ | H | T-2 | — | Q-1 | — | CO |
| 3-$CF_3$, 5-$CF_3$ | $CF_3$ | $CH_2C(O)NHCH_2CF_3$ | H | T-2 | — | Q-1 | — | CO |
| 3-$CF_3$, 5-Cl | $CF_3$ | $CH_2C(O)NHCH_2CF_3$ | H | T-2 | — | Q-1 | — | CO |
| 3-Cl, 5-Cl | $CF_3$ | — |  | T-2 | — | Q-6 | $Z^B$-7 |  |
| 3-Cl, 5-Cl | $CF_3$ | — | — | T-2 | — | Q-7 | $Z^B$-7 |  |
| 3-Cl, 5-Cl | $CF_3$ | — | — | T-2 | — | Q-5 | $Z^B$-7 |  |
| 3-Cl, 5-Cl | $CF_3$ | — | — | T-2 | — | Q-2 | $Z^D$-1 |  |
| 3-Cl, 5-Cl | $CF_3$ | $CH_2C(O)NHCH_2CF_3$ | H | T-3 | $CH_3$ | Q-1 | — | CO |
| 3-Cl, 5-Cl | $CF_3$ | $CH_2C(O)NHCH_2CC$ | H | T-3 | $CH_3$ | Q-1 | — | CO |
| 3-Cl, 5-Cl | $CF_3$ | $CH_2C(O)NHCH_2CN$ | H | T-3 | $CH_3$ | Q-1 | — | CO |
| 3-$CF_3$, 5-$CF_3$ | $CF_3$ | $CH_2C(O)NHCH_2CF_3$ | H | T-3 | $CH_3$ | Q-1 | — | CO |
| 3-Cl, 4-Cl, 5-Cl | $CF_3$ | $CH_2C(O)NHCH_2CF_3$ | H | T-3 | $CH_3$ | Q-1 | — | CO |
| 3-Cl, 4-F, 5-Cl | $CF_3$ | $CH_2C(O)NHCH_2CF_3$ | H | T-3 | $CH_3$ | Q-1 | — | CO |
| 3-Cl, 5-Cl | $CF_3$ | $CH_2C(O)NHCH_2CF_3$ | H | T-20 | — | Q-1 | — | CO |
| 3-$CF_3$, 5-$CF_3$ | $CF_3$ | $CH_2C(O)NHCH_2CF_3$ | $CH_3$ | T-20 | — | Q-1 | — | CO |
| 3-$CF_3$, 5-$CF_3$ | $CF_3$ | $CH_2C(O)NHCH_2CF_3$ | H | T-20 | — | Q-1 | — | CO |
| 3-$CF_3$, 5-$CF_3$ | $CF_3$ | $CH_2C(O)NHCH_2CF_3$ | H | T-21 | — | Q-1 | — | CO |
| 3-Cl, 5-Cl | $CF_3$ | $CH_2C(O)NHCH_2CF_3$ | H | T-21 | — | Q-1 | — | CO |
| 3-Cl, 5-Cl | $CF_3$ | $CH_2CH_2SCH_3$ | H | T-21 | — | Q-1 | — | CO |
| 3-Cl, 4-Cl, 5-Cl | $CF_3$ | $C(O)CH_3$ | H | T-22 | F | Q-1 | — | $CH_2$ |

TABLE 2-continued

| $(R^1)_n$ | $R^2$ | $R^3$ | $R^4$ | T | Y | Q | Z | X |
|---|---|---|---|---|---|---|---|---|
| 3-Cl, 4-Cl, 5-Cl | $CF_3$ | $C(O)CH(CH_3)_2$ | H | T-22 | F | Q-1 | — | $CH_2$ |
| 3-Cl, 4-Cl, 5-Cl | $CF_3$ | C(O)-cyclo-propyl | H | T-22 | F | Q-1 | — | $CH_2$ |
| 3-Cl, 4-F, 5-Cl | $CF_3$ | $C(O)CH_3$ | H | T-22 | F | Q-1 | — | $CH_2$ |
| 3-Cl, 4-Cl, 5-Cl | $CF_3$ | $C(O)CH_2CH_3$ | H | T-22 | F | Q-1 | — | $CH_2$ |
| 3-Cl, 4-F, 5-Cl | $CF_3$ | $C(O)CH_3$ | H | T-22 | Cl | Q-1 | — | $CH_2$ |
| 3-Cl, 5-Cl | $CF_3$ | $CH_2C(O)NHCH_2CF_3$ | H | T-1 | $CH_3$ | Q-1 | — | CO |
| 3-Cl, 5-Cl | $CF_3$ | $R^3$-1 (Z) | H | T-1 | $CH_3$ | Q-1 | — | CO |
| 3-Cl, 5-Cl | $CF_3$ | $R^3$-1 (E) | H | T-1 | $CH_3$ | Q-1 | — | CO |

In an embodiment an isoxazoline for use in the invention is the compound:

(Formula 2)

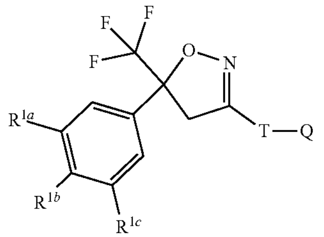

wherein $R^{1a}$, $R^{1b}$, $R^{1c}$ are independently from each other: hydrogen, Cl or $CF_3$.

Preferably $R^{1a}$ and $R^{1c}$ are Cl or $CF_3$, and $R^{1b}$ is hydrogen, T is

T-1

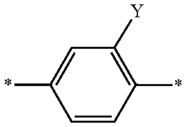

T-2

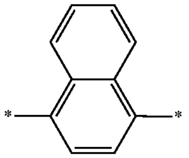

T-3

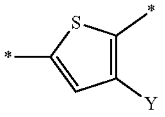

T-20

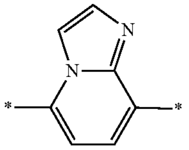

T-21

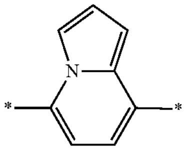

-continued

T-23

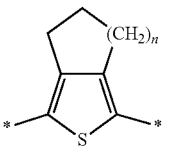

T-24

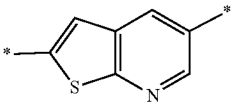

invention deliver an effective amount of the active compounds to the animal in need wherein Y is methyl, bromine, Cl, F, CN or $C(S)NH_2$; n=1 or 2; and Q is as described above.

In an embodiment of an isoxazoline as defined herein, $R^3$ is H, and $R^4$ is: $—CH_2—C(O)—NH—CH_2—CF_3$, $—CH_2—C(O)—NH—CH_2—CH_3$, $—CH_2—CH_2—CF_3$ or $—CH_2—CF_3$.

The isoxazoline for use in the invention also includes pharmaceutically acceptable salts, esters, and/or N-oxides thereof. In addition, the reference to an isoxazoline compound refers equally to any of its polymorphic forms or stereoisomers.

With respect to stereospecific forms, the pharmaceutical composition according to the invention may employ a racemic mixture of an isoxazoline for use in the invention, containing equal amounts of the enantiomers of such isoxazoline compound as described above. Alternatively, the pharmaceutical composition may use isoxazoline compounds that contain enriched stereoisomers compared to the racemic mixture in one of the enantiomers of the isoxazoline as defined herein. Also, the pharmaceutical composition may use an essentially pure stereoisomer of such isoxazoline compounds. Such enriched- or purified stereoisomer preparations of an isoxazoline for use in the invention, may be prepared by methods known in the art. Examples are chemical processes utilizing catalytic asymmetric synthesis, or the separation of diastereomeric salts (see e.g.: WO 2009/063910, and JP 2011/051977, respectively).

In an embodiment of the pharmaceutical composition according to the invention, the isoxazoline is one or more selected from the group consisting of fluralaner, afoxolaner, lotilaner or sarolaner.

In one embodiment the compound of Formula (I) is 4-[5-(3,5-Dichlorophenyl)-5-trifluoromethyl-4,5-dihydroisoxazol-3-yl]-2-methyl-N-[(2,2,2-trifluoro-ethylcarbamoyl)-methyl]-benzamide (CAS RN 864731-61-3-USAN fluralaner).

In an embodiment, the fluralaner is S-fluralaner.

In another embodiment the compound of Formula (I) is 4-[5-[3-Chloro-5-(trifluoromethyl)phenyl]-4,5-dihydro-5-

(trifluoromethyl)-3-isoxazolyl]-N-[2-oxo-2-[(2,2,2-trifluoroethyl)amino]ethyl]-1-naphthalenecarboxamide (CAS RN 1093861-60-9, USAN-afoxolaner) that was disclosed in WO2007/079162.

In an embodiment of the pharmaceutical composition according to the invention the isoxazoline is lotilaner (CAS RN: 1369852-71-0; 3-methyl-N-[2-oxo-2-(2,2,2-trifluoroethylamino)ethyl]-5-[(5S)-5-(3,4,5-trichlorophenyl)-5-(trifluoromethyl)-4H-1,2-oxazol-3-yl]thiophene-2-carboxamide).

In an embodiment of the pharmaceutical composition according to the invention the isoxazoline is sarolaner (CAS RN: 1398609-39-6; 1-(5'-((5S)-5-(3,5-dichloro-4-fluorophenyl)-5-(trifluoromethyl)-4,5-dihydroisoxazol-3-yl)-3'-H-spiro(azetidine-3,1'-(2)benzofuran)-1-yl)-2-(methylsulfonyl) ethanone).

In another embodiment, the compound of Formula (I) is (Z)-4-[5-(3,5-Dichlorophenyl)-5-trifluoromethyl-4,5-dihydroisoxazol-3-yl]-N-[(methoxyimino)methyl]-2-methylbenzamide (CAS RN 928789-76-8).

In another embodiment the compound of Formula (I) is 4-[5-(3,5-dichlorophenyl)-5-(trifluoromethyl)-4H-isoxazol-3-yl]-2-methyl-N-(thietan-3-yl)benzamide (CAS RN 1164267-94-0) that was disclosed in WO2009/0080250.

In an embodiment, the compound according to the invention is 5-[5-(3,5-Dichlorophenyl)-4,5-dihydro-5-(trifluoromethyl)-3-isoxazolyl]-3-methyl-N-[2-oxo-2-[(2,2,2-trifluoroethyl)amino]ethyl]-2-thiophenecarboxamide (CAS RN: 1231754-09-8), which was disclosed in WO 2010/070068.

In an embodiment, the implant comprises one or more additional active ingredients. In an embodiment, the additional active ingredient is a hormone or a macrocyclic lactone. In an embodiment, the macrocyclic lactone is moxidectine.

In an embodiment, the additional active ingredient is for immediate release or delayed release or both.

The implant compositions of the invention include pharmaceutically acceptable excipients. Pharmaceutically acceptable excipients include, but are not limited to, diluents, binders, surfactants, antioxidants, preservatives, pH stabilizing agents (e.g. buffers), and other non-active excipients. In another embodiment, the compositions of the invention may comprise about 0.01% to about 20% (w/w) of pharmaceutically acceptable excipients. In other embodiments, the compositions may comprise about 0.01% to about 5% (w/w), about 0.1% to about 10% (w/w) or about 0.1% to about 5% (w/w) of pharmaceutically acceptable excipients. In other embodiments the compositions may comprise about 5 to about 15% (w/w) or about 5 to about 10% (w/w) of pharmaceutically acceptable excipients. In yet another embodiment, the compositions may comprise about 7 to about 10% of pharmaceutically acceptable excipients.

Surfactants may be present in the inventive compositions at concentrations of about 0.1% to about 15% (w/w), about 1% to about 10% (w/w) or about 5% to about 10% (w/w). More typically, surfactants may be present at concentrations of about 0.1% to about 5% (w/w) or about 1 to about 5% (w/w). or about 5 to about 10% (w/w) Examples of surfactants that may be used in the compositions include, but are not limited to, glyceryl monooleate, polyoxyethylene sorbitan fatty acid esters, sorbitan esters including sorbitan monooleate (Span® 20), polyvinyl alcohol, polysorbates including polysorbate 20 and polysorbate 80, d-a-tocopherol polyethylene glycol 1000 succinate (TPGS), sodium lauryl sulfate, co-polymers of ethylene oxide and propylene oxide (e.g. poloxamers such as LUTROL® F87 and the like), polyethylene glycol castor oil derivatives including polyoxyl 35 castor oil (Cremophor® EL), polyoxyl 40 hydrogenated castor oil (Cremophor® RH 40), polyoxyl 60 hydrogenated castor oil (Cremophor® RH60); propylene glycol monolaurate (LAUROGLYCOL®); glyceride esters including glycerol caprylate/caprate (CAPMUL® MCM), polyglycolized glycerides)(GELUCIRE®, PEG 300 caprylic/capric glycerides (Softigen® 767), PEG 400 caprylic/capric glycerides (Labrasol®), PEG 300 oleic glycerides (Labrafil® M-1944CS), PEG 300 linoleic glycerides (Labrafil® M-2125CS); polyethylene glycol stearates and polyethylene glycol hydroxy stearates including polyoxyl 8 stearate (PEG 400 monostearate), polyoxyl 40 stearate (PEG 1750 monostearate, and the like). Polyethylene glycol stearates (synonyms include macrogol stearates, polyoxylstearates, polyoxyethylene stearates, ethoxylated stearates; CAS No. 9004-99-3, 9005-08-7) are mixtures of mono- and distearate esters of mixed polyoxyethylene polymers. Polyethylene glycol hydroxystearate is a mixture of mono- and diesters of hydroxystearic acid with polyethylene glycols. One polyethylene glycol hydroxystearate that may be used in the compositions is polyethylene glycol 12-hydroxystearate. In another embodiment, the inventive compositions may include the surfactant polyethylene glycol 15 12-hydroxystearate (Kolliphor® HS 15 from BASF), a mixture of mono- and diesters of 12-hydroxystearic acid with 15 moles of ethylene oxide. Again, these compounds, as well as their amounts are well known in the art. In another embodiment of the invention, the inventive compositions may include polyoxyl 35 castor oil (Kolliphor® EL) as a surfactant. In other embodiments, the inventive compositions may include polyoxyl 40 hydrogenated castor oil (Kolliphor® RH 40) or polyoxyl 60 hydrogenated castor oil as surfactants. The compositions of the invention may also include a combination of surfactants.

In an embodiment, the pharmaceutically acceptable excipient comprises a surfactant.

In an embodiment, the surfactant is micronized.

In an embodiment, the surfactant is extra granular.

In an embodiment, the surfactant is intra granular.

In an embodiment, the surfactant is a poloxamer. In an embodiment the surfactant is a nonionic surfactant such as a fatty alcohol, glyceryl esters, fatty acid esters of fatty alcohols and other alcohols. In an embodiment, the surfactant is a poloxamer, polyoxy 40 stearate, polyethylene glycol, propylene glycol, sorbitan, sucrose, cholesterol, lauryl alcohol, cetyl alcohol, stearyl alcohol or mixtures thereof.

In an embodiment, the poloxamer is micronized.

In an embodiment, the size of the micronized poloxamer is about 5 μm, about 10 μm, about 15 μm, about 20 μm, about 25 μm, about 30 μm, about 35 μm, or about 40 μm.

In an embodiment, the poloxamer is extra granular.

In an embodiment, the poloxamer is intra granular.

In an embodiment, the pellets further comprise additional excipients.

In an embodiment, the pharmaceutically acceptable excipient comprises a diluent.

In an embodiment, the diluent is selected from the group consisting of lactose, mannitol, sorbitol sucrose, dextrose, starches, hydrolyzed starches and combinations thereof.

In an embodiment, the diluent is a sugar. In an embodiment, the diluent is lactose. In an embodiment, the binder is dicalcium phosphate, calcium sulfate, cellulose, kaolin, mannitol, sodium chloride, dry starch, powdered sugar, sorbitol, sucrose, inositol, bentonite, amine slats of lactose, microcrystalline cellulose, corn starch, hydroxypropylmethylcellulose (HPMC) or mixtures thereof.

In an embodiment, the pharmaceutically acceptable excipient comprises a binder.

In an embodiment, the binder is povidone (poly vinylpyrrolidone). In an embodiment, the binder is starch, gelatin and sugars such as sucrose, glucose, dextrose and molasses. In embodiment, the binder is a natural or synthetic gum such as acacia, sodium alginate, carboxymethyl cellulose, methylcellulose, and Veegum. In an alternative embodiment, the binder is polyethylene glycol, ethylcellulose or waxes. Mixtures of any of the aforementioned binders are also an embodiment.

In an embodiment, the pharmaceutically acceptable excipient comprises a lubricant.

In an embodiment, the lubricant is magnesium stearate. In an embodiment the lubricant is calcium stearate, stearic acid, hydrogenated vegetable oils, polyethylene glycol (PEG) or mixtures thereof.

In an embodiment, the pharmaceutically acceptable excipient comprises a disintegrant.

In an embodiment, the disintegrant is sodium starch glycolate. In an embodiment, the disintegrant is at a starch, a cross-linked starch, a clay, a cellulose, a cross-linked cellulose, an algin, a gum or a cross-linked polymer or mixtures thereof. In an embodiment, the disintegrant is corn starch, potato starch, croscarmelose or crospovidone.

In an embodiment, the pharmaceutically acceptable excipient comprises an anti-tacking agent.

In an embodiment, the anti-tacking agent is selected from the group consisting of silicon dioxide, fumed silica, talc, and magnesium carbonate.

The inventive compositions may contain other inert ingredients such as antioxidants, preservatives, or pH stabilizers. These compounds are well known in the composition art. Antioxidants such as vitamin E, alpha tocopherol, ascorbic acid, ascorbyl palmitate, citric acid, fumaric acid, malic acid, sodium ascorbate, sodium metabisulfate, sodium metabisulfite, n-propyl gallate, BHA (butylated hydroxy anisole), BHT (butylated hydroxy toluene), BHA and citric acid, monothioglycerol, tert-butyl hydroquinone (TBHQ), benzyl alcohol and the like, may be added to the present composition. The antioxidants are generally included in the compositions of the invention in amounts of about 0.01% to about 3%, or from about 0.01 to about 2% (w/w), based upon total weight of the composition (w/w). In another embodiment, the compositions contain about 0.05 to about 1.0% (w/w) of one or a mixture of antioxidants.

Preservatives, such as benzyl alcohol, are suitably used in the composition in amounts ranging from about 0.01 to about 10.0%, with about 0.05 to about 5.0% being especially preferred. Other preservatives include parabens (methylparaben and/or propylparaben), benzalkonium chloride, benzethonium chloride, benzoic acid, benzyl alcohol, bronopol, butylparaben, cetrimide, chlorhexidine, chlorobutanol, chlorocresol, cresol, ethylparaben, imidurea, methylparaben, phenol, phenoxyethanol, phenylethyl alcohol, phenylmercuric acetate, phenylmercuric borate, phenylmercuric nitrate, potassium sorbate, sodium benzoate, sodium propionate, sorbic acid, thimerosal, and the like. Preferred ranges for these compounds include from about 0.01 to about 5%.

Compounds which stabilize the pH of the composition may also be present. Again, such compounds are well known to a practitioner in the art as well as how to use these compounds. Buffering systems include, for example, systems selected from the group consisting of acetic acid/acetate, malic acid/malate, citric acid/citrate, tartaric acid/tartrate, lactic acid/lactate, phosphoric acid/phosphate, glycine/glycimate, tris, glutamic acid/glutamates and sodium carbonate, especially sodium phosphate or sodium citrate.

In an embodiment, the implant comprises one or more immediate release pellets and one or more delayed release pellets.

In an embodiment, the ratio of the immediate release pellets to the delayed release pellets is between about 1:10 and about 10:1. In an embodiment, the ratio of the immediate release pellets to the delayed release pellets is between about 1:5 and about 5:1. In an embodiment, the ratio of the immediate release pellets to the delayed release pellets is about 1:1.

In an embodiment, the percentage of fluralaner in each pellet is between about 50% w/w to about 90% w/w. In an embodiment, the percentage of fluralaner in each pellet is between about 60% w/w to about 80% w/w. In an embodiment, the percentage of fluralaner in each pellet is between about 65% w/w to about 75% w/w.

In an embodiment, the delayed release pellets are coated with a biodegradable polymer.

In an embodiment, the biodegradable polymer is chosen from poly(lacdic-co-glycolic acid) (PLGA) and polycaprolactone (PCL).

In an embodiment, the biodegradable polymer is poly(lactic-co-glycolic acid) (PLGA).

In an embodiment, the ratio of the lactic acid and glycolic acid monomers in the PLGA is about 50:50 to about 90:10.

In an embodiment, the ratio of the lactic acid and glycolic acid monomers in the PLGA is 65:35.

An embodiment of the invention is an implant for the control of external parasites in livestock comprising 8-10 pellets wherein the pellets are a mixture of immediate release pellets and delayed release pellets, wherein

- a) the immediate release pellets comprise
  - i) an isoxazoline compound of formula (I), especially fluralaner
  - ii) one or more pharmaceutically acceptable excipients and
  - iii) micronized poloxamer, and
- b) the delayed release pellets comprise
  - i) an isoxazoline compound of formula (I), especially fluralaner
  - ii) one or more pharmaceutically acceptable excipients, wherein the ratio of the immediate release pellets and the delayed release pellets is between 1:10 and 10:1.

In an embodiment, the delayed release pellets are coated with PLGA 65:35.

An embodiment of the invention is a method of treating or preventing a parasite infestation in livestock animals comprising administering any of the implants disclosed herein.

In an embodiment, the animals are bovids, such as cattle.

In an embodiment, the animals are sheep, goats or pigs.

In an embodiment, the animal is a companion animal. In an embodiment the animal is a dog or a cat.

In an embodiment, the implant is initially effective after implantation as early as 1 day, 7 days, 10 days, 2 weeks, 3 weeks, or one month.

In an embodiment, the implant is effective for at least 2 months or at least 3 months or at least 4 months or at least 5 months or at least 6 months or at least 9 months or at least 1 year.

In an embodiment, the administration of the implant is through injection.

In an embodiment, the parasite is an ectoparasite.

In another aspect of the invention, a method for preventing or treating a parasite infestation/infection in an animal is provided, comprising administering to the animal an implantable composition comprising an effective amount of at least one isoxazoline active agent together with a pharmaceutically acceptable excipient that is suitable for implanting into the animal. The compositions or compositions of the invention have long-lasting efficacy against ectoparasites (e.g. fleas, lice and ticks) and in certain embodiments may also active against endoparasites that harm animals.

In one embodiment of the invention, methods for the treatment or prevention of a parasitic infestation or infection in a domestic animal are provided, which comprise administering an implant composition comprising an effective amount of at least one isoxazoline active agent to the animal. Ectoparasites against which the methods and compositions of the invention are effective include, but are not limited to, fleas, ticks, mites, mosquitoes, flies and lice. In certain embodiments wherein the compositions include one or more additional active agents that are active against internal parasites the compositions and methods of the invention may also effective against endoparasites including, but not limited to, cestodes, nematodes, hookworms and roundworms of the digestive tract of animals and humans.

The ectoparasites treated include but are not limited to fleas, ticks, mites, mosquitoes, flies, screw worms, lice, blowfly and combinations thereof.

In another embodiment for the treatment against ectoparasites, the ectoparasite is from a tick from the genera *Boophilus/Rhipicephalus, Dermacentor, Ixodes, Boophilus, Ambylomma, Haemaphysalis, Hyalomma* especially *Boophilus*(*Rhipicephalus*), especially those of the species *microplus* (cattle tick), *R. decoloratus* and *R. annulatus.*

*Rhipicephalus microplus, R. decoloratus* and *R. annulatus* are single host ticks, this means all three stages of the lifecycle are spent on the same animal.

Multi-host ticks means the tick drops to the ground after each stage and the re-attaches to another host and the species of host between the different stages may differ are e.g. *Amblyoma cajennense, Ixodes holocyclus*, i.e. paralysis tick: *H. longicornis: Rhipicephalus appendiculatus* and *Amblyoma haebraum, Dermacentor albipictus, Amblyoma, maculatum, Amblyoma andersoni, Ixodes ricinus, Dermacentor marginatus.*

Additional examples of ectoparasites include but are not limited to flies causing myiases such as *Dermatobia hominis* (known as Berne in Brazil) and *Cochliomyia hominivorax* (greenbottle); sheep myiases such as *Lucilia sericata, Lucilia cuprina* (known as blowfly strike in Australia, New Zealand and South Africa).

Biting flies namely those whose adult constitutes the parasite, such as *Haematobia irritans* (horn fly), *Haematobia irritans* exiqua (buffalo fly) and *Stomoxys calcitrans* (stable fly).

Sucking lice consume a blood meal from their host and are more important in transmitting pathogens. Chewing or biting lice ingest fur and skin and sometimes blood from their host; important lice parasites are the cattle biting louse (*Bovicola bovis*), the longnosed cattle louse (*Linognathus vituli*), the little blue cattle louse (*Solenopotes capillatus*), the shortnosed cattle louse (*Haematopinus eurysternus*), and the cattle tail louse (*Haematopinus quadripertusus*) and the sheep biting louse of sheep and goats (*Bovicola ovis*).

Important mite parasites are e.g. Chorioptes *bovis, Sarcoptes scabiei* and *Psoroptes ovis.*

The above list is not exhaustive and other ectoparasites are well known in the art to be harmful to animals, especially livestock animals, especially ruminants, more especially cattle or sheep. These include, for example migrating dipterous larvae.

In some embodiments of the invention, especially in case the isoxazoline compound is combined with another active ingredient, the composition can also be used to treat against endoparasites such as those helminths selected from the group consisting of *Anaplocephala, Ancylostoma, Anecator, Ascaris, Capillaria, Cooperia, Dipylidium, Dirofilaria, Echinococcus, Enterobius, Fasciola, Haemonchus, Oesophagostumum, Ostertagia, Toxocara, Strongyloides, Toxascaris, Trichinella, Trichuris*, and *Trichostrongylus*, among others.

In another preferred embodiment, the methods and compositions of the invention are used for the treatment or prevention of parasitic infections and infestations in cattle or sheep. When treating livestock animals such as cattle or sheep, the methods and compositions are particularly effective against *Rhipicephalus* (*Boophilus*) *microplus, Haematobia irritans* (horn fly), *Stomoxys calcitrans* (stable fly), *Bovicola bovis* and *B. ovis* and sheep myiases such as *Lucilia sericata*, (European green blowfly), *Lucilia cuprina* (Green blowfly or Australian sheep blowfly known as blowfly strike in Australia, New Zealand and South Africa) *Chrysomya* rufifacies (Hairy maggot fly), *Chrysomya varipes* (Small green blowfly), *Calliphora stygia* (Common brown blowfly), *Calliphora* augur (Lesser brown blowfly (eastern), *Calliphora novicia* (Lesser brown blowfly (western).

Important lice species in ruminant animals are *Bovicola* spp. and *Linognathus* spp (e.g. *Bovicola ovis*).

The terms "treating" or "treat" or "treatment" are intended to mean the application or administration of a composition of the invention to an animal that has a parasitic infestation for the eradication of the parasite or the reduction of the number of the parasites infesting the animal undergoing treatment. It is noted that the compositions of the invention may be used to prevent such a parasitic infestation.

The compositions of the invention are administered in (parasiticidally) effective amounts which are which are suitable to control the parasite in question to the desired extent. By "effective amount" is intended a sufficient amount of a composition of the invention to eradicate or reduce the number of parasites infesting the animal. In some embodiments, an effective amount of the active agent achieves at least 70% efficacy against the target parasite. In other embodiments, an effective amount of the active agent achieves at least 80%, or at least 90% efficacy against the target pests. Preferably, an effective amount of the active agent will achieve at least 95%, at least 98% or 100% efficacy against the target parasites.

In each aspect of the invention, the compounds and compositions of the invention can be applied against a single parasite or combinations thereof.

The compositions of the invention may be administered continuously, for treatment or prevention of parasitic infections or infestations. In this manner, the compositions of the invention deliver an effective amount of the active compounds to the animal in need thereof to control the target parasites.

EXAMPLES

Example 1—Implant Pellet Formulations

| | Group | | | | | | | |
|---|---|---|---|---|---|---|---|---|
| | 1A | 1B | 1C | 1D | 1E | 1F | 1G (delayed Release) | 1H Immediate release) |
| Subject | 1 to 6 | 7 to 12 | 13 to 18 | 19 to 24 | 25 to 30 | 31 to 36 | | |
| Fluralaner (micronized)* | 70.0 | 70.0 | 70.0 | 70.0 | 70.0 | 70.0 | 80.0 | 71.7 |
| Lactose* | 13.5 | 13.5 | 13.5 | 18.5 | 13.5 | 13.5 | 14.0 | 13.4 |
| Povidone USP* | 5.0 | 5.0 | 5.0 | 5.0 | 5.0 | 5.0 | 4.0 | 3.6 |
| Micronized Poloxamer 188/F68* | / | / | 9.0 | / | / | / | / | 9.0 |
| Non-micronized Poloxamer 188/F68* | 9.0 | 9.0 | | 4.0 | / | / | / | / |
| Micronized Poloxamer 407/127* | / | / | / | / | 9.0 | / | / | / |
| Polyoxyl 40 stearate granular* | / | / | / | / | / | 9.0 | / | / |
| Magnesium stearate* | / | 2.5 | 2.5 | 2.5 | 2.5 | 2.5 | 2.0 | 2.2 |
| Fluralaner/implant | 32 mg | 32 mg | 32 mg | 32 mg | 32 mg | 32 mg | 34 mg | 30 mg |
| Order of addition of surfactant | Extragranular | Extragranular | Intragranular | Extragranular | Intragranular | Extragranular | | Extragranular |

*Quantities given in % w/w

Formulation 1A: Povidone was dissolved in water to obtain a 20% w/w aqueous solution of povidone. A small portion of the non-micronized Poloxamer 188 (0.5% w/w) was dissolved in povidone solution to form the binder solution. In a separate beaker, fluralaner and lactose were blended with a spatula to form the powder blend. The binder solution containing povidone and poloxamer was slowly added to the powder blend and mixed with a spatula to obtain granules. The wet granules were dried in an oven at 50° C. for 18 hours. The dry granules were milled using a mortar pestle and passed through 18 mesh screen. The dried and sieved granules were then blended with the remaining 8.5% non-micronized Poloxamer 188. The blend was compressed into pellets using a Carver press with ⅛" B tooling. The pellets were compressed using 0.5 metric tons force. The target weight of pellets was 45.8 mg for a concentration of 32 mg fluralaner/pellet, target hardness 4-10 kP (See U.S. Pharmacopeia Convention, 2011, Chapter 1217). The diameter and length of pellets were 3 mm and 4.6 mm, respectively. Total batch size was 20 g.

Formulation 1B: Pellets prepared as described in Formulation 1A. Magnesium stearate was added with the remaining Poloxamer 188. Pellet weight, dimensions and hardness were same as the Formulation 1A pellets.

Formulation 1C: Povidone was dissolved in water to obtain a 20% w/w aqueous solution of povidone. A small portion of the micronized Poloxamer 188 (0.5% w/w) was dissolved in povidone solution to form the binder solution. In a separate beaker, fluralaner, lactose and the remaining 8.5% w/w of the micronized Poloxamer 188 were blended with a spatula to form the powder blend. The binder solution containing povidone and poloxamer was slowly added to the powder blend and mixed with a spatula to obtain granules. The wet granules were dried in an oven at 50° C. for 18 hours. The dry granules were milled using a mortar pestle and passed through 18 mesh screen. The dried and sieved granules were then blended with magnesium stearate and compressed into pellets using a Carver press with ⅛" B tooling. The pellets were compressed using 0.5 metric tons force. The target weight of pellets was 45.8 mg for a concentration of 32 mg fluralaner/pellet, target hardness 4-10 kP (See U.S. Pharmacopeia Convention, 2011, Chapter 1217). The diameter and length of pellets were 3 mm and 4.6 mm, respectively.

Formulation 1D: Pellets prepared as described in Formulations 1A and 1B. Pellet weight, dimensions and hardness same as the Formulation 1A pellets.

Formulation 1E: Pellets prepared as described in Formulation 1C. Pellet weight, dimensions and hardness same as the Formulation 1C pellets.

Formulation 1F: Pellets prepared as described in Formulations 1A and 1B. Pellet weight, dimensions and hardness same as the Formulation 1A pellets.

Formulation 1G: Fluralaner and lactose were blended in a beaker to form a powder blend using a spatula. In a separate beaker, povidone was dissolved in water. The resulting povidone solution was slowly added to the powder blend while mixing with a spatula. Povidone was used as a binder to agglomerate the powder to obtain wet granules. Granules were dried at 60° C. overnight (~24 hours). The dried granules were passed through 18 mesh screen and blended with magnesium stearate. The blend was compressed into pellets using a Carver press with ⅛" B tooling at a target weight of 42 mg/pellet to yield 34 mg fluralaner/pellet. Total batch size was 20 g.

Formulation 1H: Fluralaner and lactose were blended in a beaker using a spatula to form a powder blend. In a separate beaker, povidone was dissolved in water. Povidone solution was slowly added to the powder blend while mixing with a spatula. Povidone was used as a binder to agglomerate the powder to obtain wet granules. Granules were dried at 60° C. overnight (~24 hours). The dried granules were passed through 18 mesh screen and blended with micronized Poloxamer 188 and magnesium stearate. The blend was compressed into pellets using a Carver press with ⅛" B tooling at a target weight of 42 mg/pellet to yield 30 mg fluralaner/pellet. Total batch size was 20 g.

Example 2: Pharmacokinetic (PK) Study of the Formulations of Example 1

The study was conducted as a multisite, randomized, non-blinded study, using a parallel design. The six beef cattle that were assigned to each group 1A-1H were treated once subcutaneously with an ear implant at the dose of 1.0 mg fluralaner/kg body weight (BW). Then, blood samples were collected over an 84-day period. PK results for Groups 1A-1F were a part of a separate study than Group 1G (delayed release) and 1H (immediate release). However, plasma concentration of s-fluralaner following implant administration from both of these studies are presented in FIG. 1. S-fluralaner is the active enantiomer of fluralaner.

Groups 1A, 1B, 1D and 1F did not release fluralaner above a level that would indicate efficacy against the targeted ectoparasite species. Formulations 1A and 1B contain non-micronized Poloxamer 188 which was added extragranular whereas Group 1C animals received a formulation containing micronized Poloxamer 188 which was added intragranular. Group 1H animals received formulation containing micronized Poloxamer 188 which was added extragranular. Comparing PK profiles of group 1B and group 1H animals it can be concluded that micronized Poloxamer 188 improves fluralaner release from implants. Group 1E and 1C animals show similar PK profiles. The difference between the formulations dosed to Groups 1C and 1E animals is that Group 1C animals received formulation containing micronized poloxamer 188 whereas Group 1E animals received formulation prepared with micronized poloxamer 407. Fluralaner release from implants containing Poloxamer 188 and 407 was similar. No improvement in fluralaner release was observed by replacing poloxamer 188 with poloxyl 40 stearate in Group 1F animals (compare group 1B and 1F). Group 1D animals received a formulation with lower concentration of poloxamer 188. Comparing Group 1B and 1D animals, it can be concluded that there was no impact of lowering the concentration of non-micronized poloxamer 188 on fluralaner release.

Group 1H animals received formulation containing micronized Poloxamer 188 whereas group 1G animals received formulation without Poloxamer 188. Inclusion of poloxamer 188 improved fluralaner release from the implants. The combined administration of the immediate release pellets (1H) and delayed release pellets (1G) produced fluralaner blood levels above a level that would indicate efficacy against the targeted parasite species in less than 7 days and maintained the fluralaner blood level at least that level beyond 90 days. This indicates that an implant combining both of these pellets would have both rapid on set efficacy and long term efficacy against the targeted parasites.

Example 3—Additional Implant Pellet Formulations

Table 3 shows formulations prepared to evaluate the effect of different excipients on PK, the effect of formulation scale-up on PK and the effect of coating the pellets with PLGA on extended release.

TABLE 3

| | Formulation | | | | | | |
|---|---|---|---|---|---|---|---|
| Ingredients | 3A Conc. (% w/w) | 3B Conc. (% w/w) | 3C Conc. (% w/w) | 3D Conc. (% w/w) | 3E Conc. (% w/w) | 3F Conc. (% w/w) | 3G Conc. (% w/w) |
| Fluralaner (micronized) | 70 | 70 | 70 | 70 | 65.7 | 65.7 | 70 |
| Lactose | 11.5 | 13.5 | 13.5 | 13.5 | 12.7 | 12.7 | 13.5 |
| Povidone | 5 | 3 | 5 | 5 | 4.7 | 4.7 | 5 |
| Pluronic F68 (micronized) | 9 | 6 | 9 | 9 | 8.5 | 8.5 | 9 |
| Magnesium Stearate | 2.5 | 2.5 | 2.5 | 2.5 | 2.5 | 2.5 | 2.5 |
| PEG8000 | | 5 | | | | | |
| Sodium starch glycolate | 2 | | | | | | |
| PLGA 65:35 | | | | | 5.9 | 5.9 | |
| Silicon dioxide | | | | | 0.2 | 0.2 | |
| | 100 | 100 | 100 | 100 | 100 | 100 | 100 |

The method of preparation of the various batches is described below:

An aqueous binder solution containing povidone and 0.5% w/w pluronic F68 (poloxamer 188) was prepared for all batches by dissolving povidone and poloxamer in water. Micronized pluronic F68 (poloxamer 188) was used in all formulations in the new PK study because the release of fluralaner was better from Formulation 1C in comparison to Formulation 1B in PK study of Example 2 above.

Formulation 3A: In a mortar pestle, lactose, half of the total amount of sodium starch glycolate (SSG), poloxamer 188 and fluralaner were blended together. The powder blend was granulated with binder solution. The wet granules were dried at 60° C. for 24 hours. The dried granules were milled with a mortar pestle and sieved through 18 mesh screen. The granules were blended with the remaining half amount of SSG and magnesium stearate. The final blend was compressed into pellets.

Formulation 3B: In a mortar pestle, lactose, 40% of the total amount of polyethylene glycol 8000 (PEG8000), poloxamer 188 and fluralaner were blended together. The powder blend was granulated with binder solution containing povidone, 40% of total amount of polyethylene glycol 8000 and 0.5% w/w poloxamer 188. The wet granules were dried at 40° C. for 24 hours. The dried granules were milled with a mortar pestle and sieved through 18 mesh screen. The granules were blended with the remaining 20% of PEG8000 and magnesium stearate. The final blend was compressed into pellets.

Formulation 3G: The formulation is same as Formulation 1C except that 50% of poloxamer 188 was added intragranular (before adding binder solution) and remaining 50% was added extragranular (after granules were prepared).

Formulations 3A, 3B and 3G were compressed into pellets using a compression simulator with ⅛" B tooling. The compression force of 1-2 kN was used to manufacture pellets with a weight of 45-50 mg, hardness of 4-10 kP, 3 mm in diameter and 4.6 mm in height. Total batch sizes were 20 g.

Formulation 3C: The formulation and process of preparation were same as Formulation 1C except that Formulation 3C was scaled-up in a high shear wet granulator. The total batch size was 500 g.

Formulation 3D: This batch was prepared as Formulation 1B except the total batch size was 500 g.

Formulations 3E and 3F: Pellets were prepared as in Formulations 3C and 3D respectively. The each pellet was coated with PLGA 65:35 to produce Formulations 3E and 3F, respectively. Therefore, Formulation 3E corresponds to a coated pellet of Formulation 3C and Formulation 3F corresponds to a coated pellet of Formulation 3D. PLGA 65:35 was dissolved in acetone. 0.2% w/w silicon dioxide was dispersed in PLGA/acetone solution. Silicon dioxide was added to prevent the pellets from sticking to each other after coating. The pellets were loaded into the coating bowl of Caleva minicoater. The pellets were fluidized and the PLGA solution was sprayed onto the pellets at room temperature. The acetone evaporated leaving a coating of PLGA onto the pellets.

Example 4: Pharmacokinetic (PK) Study of the Formulations of Example 3

Figure 3:
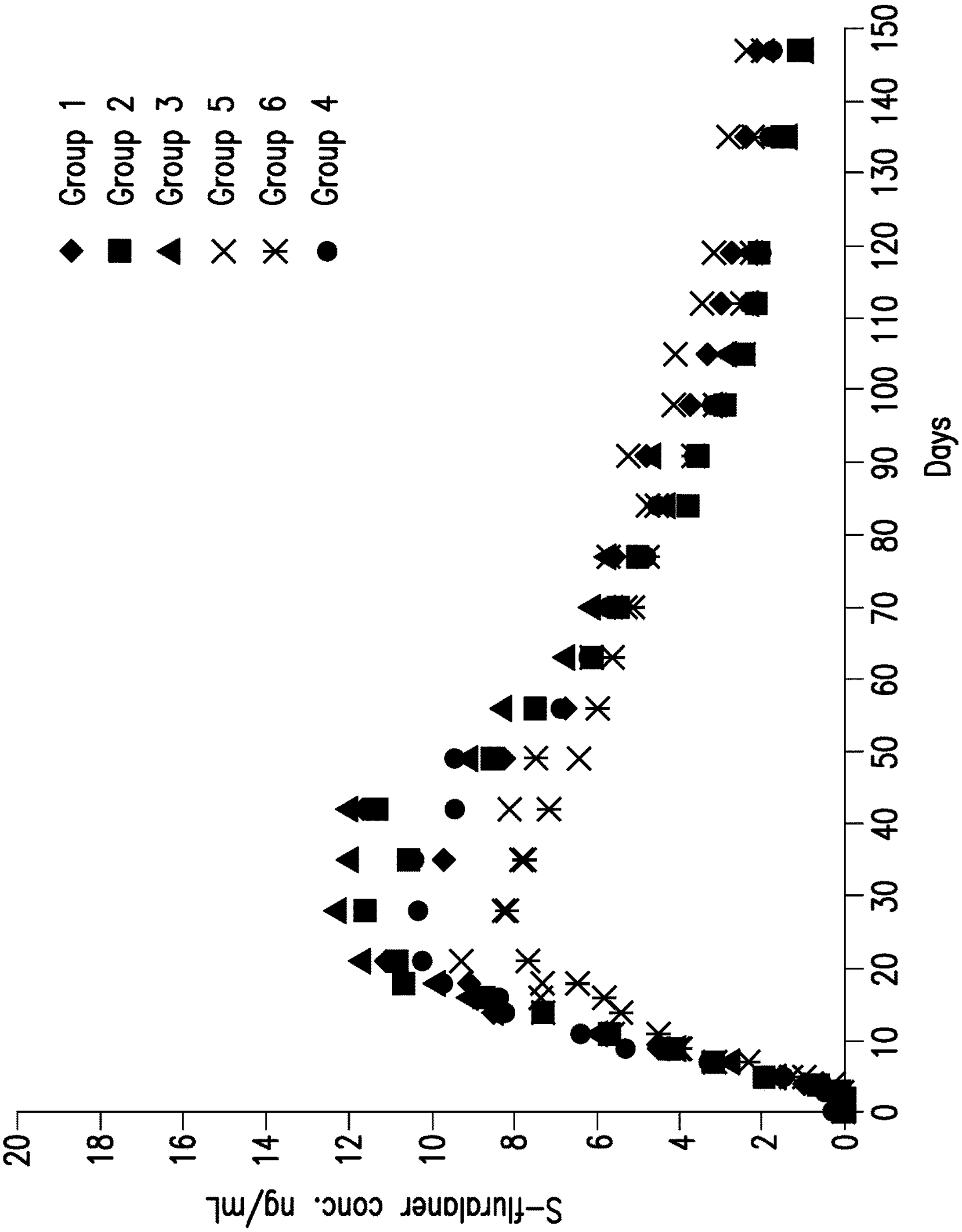

The study was conducted as a multisite, randomized, non-blinded study, using a parallel design. The six beef cattle that were assigned to each group 3A-3G were treated once subcutaneously with an ear implant at the dose of 1.0 mg fluralaner/kg body weight (BW). Then, blood samples were collected over a 147-day period. Plasma concentration of s-fluralaner following implant administration from this study is presented in FIG. 3. S-fluralaner is the active enantiomer of fluralaner.

A mixture of uncoated and coated pellets were tested in this PK study. The dosing plan is given below:

1. Group 1: Each animal received 5 uncoated pellets from Formulation 3A and 5 coated pellets from Formulation 3E.
2. Group 2: Each animal received 10 pellets from Formulation 3B.
3. Group 3: Each animal received 10 pellets from Formulation 3G.
4. Group 4: Each animal received 10 pellets from Formulation 3C.
5. Group 5: Each animal received 5 uncoated pellets from Formulation 3C and 5 coated pellets from Formulation 3E.
6. Group 6: Each animal received 5 uncoated pellets from Formulation 3D and 5 coated pellets from Formulation 3F.

All groups 1-6 released fluralaner above a level that would indicate efficacy against the targeted ectoparasite species. There were no significant differences between the various formulations. Groups 5 and 1 released fluralaner slightly above efficacy level up to 147 days. By adding 21 days to complete duration of tick life cycle an efficacy of approximately 6 months can be achieved with groups 1 and 5. Group 1 received 5 uncoated pellets from formulation 3A and 5 coated pellets from formulation 3E whereas Group 5 received 5 uncoated pellets from formulation 3C and 5 coated pellets from formulation 3E. The uncoated pellets in Group 1 contain a superdisintegrant which aids faster breakage of pellets leading to higher fluralaner release in 2 weeks. Group 5 also has a desirable release onset in 2 weeks indicating that it is not necessary to include a superdisintegrant in the pellets. Moreover, Group 5 pellets would be preferred because uncoated (Formulation 3C) and coated pellets (Formulation 3E) contain the same core pellet.

Group 6 released fluralaner only slight below efficacy level on day 147. Group 6 also received 5 coated (Formulation 3F) and 5 uncoated pellets (Formulation 3D) but the pellets contained extragranular Poloxamer 188 whereas Group 5 pellets had intragranular Poloxamer 188. PK profile of Group 5 is only slightly better than Group 6 indicating addition of Poloxamer 188 intragranular would be preferred. Group 4 received 10 uncoated pellets with intragranular Poloxamer 188. Comparing PK profiles of Groups 5 and 4 suggests that coated pellets helped with sustained fluralaner release after 120 days. No improvement in fluralaner release was observed by using a mixture of intragranular and extragranular Poloxamer 188 (compare Group 4 and 3) versus using intragranular Poloxamer 188 alone. Addition of PEG8000 in formulation 3B (Group 2) did not help with sustained release. This PK study indicates that an implant combining both uncoated and coated pellets would have both rapid on set efficacy and long term efficacy against targeted parasites.

What is claimed is:

1. A method of treating a parasite infestation in livestock animals comprising administering an implant to animals in need thereof wherein the implant comprises one or more immediate release pellets and one or more delayed release pellets, wherein the ratio of the immediate release pellets and the delayed release pellets is between 1:10 and 10:1 and wherein a) the immediate release pellets comprise
   i) fluralaner
   ii) diluent;
   iii) binder and
   iv) micronized intragranular poloxamer, and
b) the delayed release pellets comprise
   i) fluralaner
   ii) diluent, and
   iii) binder;

wherein the delayed release pellets are coated with a biodegradable polymer.

2. The method of claim 1, wherein the implant is effective for at least 3 months.

3. The method of claim 1, wherein the diluent is lactose.

4. The method of claim 1, wherein the binder is povidone.

5. The method of claim 1, wherein the percentage of fluralaner in each pellet is between about 50% w/w to about 90% w/w.

6. The method of claim 1, wherein the ratio of the immediate release pellets to delayed release pellets is about 1:1.

7. The method of claim 1, wherein the biodegradable polymer is chosen from poly(lactic-co-glycolic acid) (PLGA) and polycaprolactone (PCL).

8. The method of claim 1, wherein the biodegradable polymer is poly(lactic-co-glycolic acid) (PLGA) and the ratio of the lactic acid and glycolic acid monomers in the PLGA is about 50:50 to about 90:10.

9. The method of claim 1, wherein the delayed release pellets are coated with PLGA 65:35.

* * * * *